United States Patent
Wesley (10) Patent No.: US 6,298,347 B1
(45) Date of Patent: Oct. 2, 2001

(54) SYSTEM AND METHOD FOR REMOTE DATA ENTRY

(75) Inventor: Daniel Wesley, Bryn Mawr, PA (US)

(73) Assignee: Numoda Corporation, Philadelphia, PA (US)

( * ) Notice: Subject to any disclaimer, the term of this patent is extended or adjusted under 35 U.S.C. 154(b) by 0 days.

(21) Appl. No.: 09/139,318

(22) Filed: Aug. 25, 1998

(51) Int. Cl.[7] .................................................. G06F 17/30
(52) U.S. Cl. .......................... 707/10; 707/506; 707/104; 707/203; 705/1; 705/26; 379/110
(58) Field of Search .......................... 707/3, 5, 10, 102, 707/203, 104; 379/92.03, 110.01; 705/26, 1

(56) References Cited

U.S. PATENT DOCUMENTS

| | | | |
|---|---|---|---|
| 4,905,080 | * 2/1990 | Watanabe et al. | 358/84 |
| 5,379,213 | * 1/1995 | Derks | 364/411 |
| 5,570,415 | * 10/1996 | Stretton et al. | 379/110 |
| 5,857,201 | * 6/1999 | Wright, Jr. et al. | 707/104 |
| 5,870,765 | * 2/1999 | Bauer et al. | 707/203 |
| 5,873,086 | * 2/1999 | Fujii et al. | 707/10 |
| 5,950,173 | * 9/1999 | Perkowski | 705/28 |
| 5,999,908 | * 12/1999 | Abelow | 705/1 |
| 6,058,393 | * 2/2000 | Meier et al. | 707/10 |
| 6,065,008 | * 5/2000 | Simon et al. | 707/10 |
| 6,067,523 | * 5/2000 | Bair et al. | 705/3 |

\* cited by examiner

*Primary Examiner*—Hosain T. Alam
*Assistant Examiner*—Anh Ly
(74) *Attorney, Agent, or Firm*—Akin, Gump, Strauss, Hauer & Feld, L.L.P.

(57) ABSTRACT

Uniformly formatted sets of data are collected from a remote site and electronically transmitted back to a central collection site. In this process, data to be collected is specified. Then, a questionnaire specification file is generated. The questionnaire specification file defines the file specification and associated data structure for creating questionnaires. A telecommunications link is established between a central computing/data processing unit at the central collection site and a remote computing/data processing unit at the remote site. The questionnaire specification file is electronically transmitted to the remote data processing unit. In the remote unit, the defined file specification and associated data structure in the questionnaire specification file is used to create at least one questionnaire. The questionnaire is completed at the remote site by entering questionnaire data into the remote unit. The data is then transmitted in report format back to the central unit at the central collection site.

37 Claims, 8 Drawing Sheets

Microfiche Appendix Included
(2 Microfiche, 122 Pages)

HEALTH DELIVERY ORGANIZATION
LONG TERM CARE (SNF)
SITE VISIT TOOL

PHILADELPHIA, PA                                          JANUARY 1997

| SOURCE V W | CRITERIA # | RECOMMENDED CRITERIA – PART 2 | Doc in Policy/MR Practice or N/A | Doc in Policy Only | Doc in MR or Prac Only | Not Doc |
|---|---|---|---|---|---|---|
| | | SECTION 4 – Environment of Care – Design of Management Plans | | | | |
| | 4BR1 | Safety management plan is documented. | | | | |
| | 4BR2 | Hazardous materials and wastes management plan is documented. | | | | |
| | 4BR3 | Emergency preparedness management plan addresses is documented. | | | | |
| | 4BR4 | Life safety management plan is documented. | | | | |
| | 4BR5 | Medical equipment management plan is documented. | | | | |
| | 4BR6 | Utilities system management plan is documented. | | | | |
| | | Implementation | | | | |
| | 4CR1 | Orientation, education and assessment of the staff abilities to perform responsibilities is documented. | | | | |
| | 4CR2 | Implementation of the emergency preparedness management plan is documented. | | | | |
| | 4CR3 | Implementation of the life-safety management plan is documented. | | | | |
| | 4CR4 | Implementation of the medical equipment management plan is documented. | | | | |
| | 4CR5 | Implementation of the utilities management plan is documented. | | | | |

*Fig. 3b*

PHILADELPHIA, PA

HEALTH DELIVERY ORGANIZATION
LONG TERM CARE (SNF)
SITE VISIT TOOL

JANUARY 1997

| SOURCE V W | CRITERIA # | RECOMMENDED CRITERIA – PART 2 | Doc in Policy/MR Practice or N/A | Doc in Policy Only | Doc in MR or Prac Only | Not Doc |
|---|---|---|---|---|---|---|
| | | Implementing Maintenance, Testing, and Inspection of the Operational Components of Plans Measurement Systems | | | | |
| | 4ER1 | Analysis of identified environment of care safety management issues and development of recommendations is documented. | | | | |
| | 4ER2 | Safety officer to implement recommendations and monitor their effectiveness is documented. | | | | |
| | | Social Environment | | | | |
| | 4FR1 | Space to support the services is documented. | | | | |
| | 4FR2 | An environment that fosters a positive self-image for the resident and preserves his or her human dignity is documented. | | | | |
| | 4FR3 | Privacy for the resident is documented. | | | | |
| | 4FR4 | Activities to support developing and maintaining the resident's interests, skills, and opportunities for personal growth are documented. | | | | |

NA = Service or Procedure not Provided
V = Verbal
W = Written

SYSTEM AND METHOD FOR REMOTE DATA ENTRY

REFERENCE TO MICROFICHE APPENDIX

This application includes a microfiche appendix of two (2) sheets of microfiche having a total of 122 frames.

FIELD OF THE INVENTION

The present invention relates to data processing systems and methods for collecting data from remote sites and transmitting the data to a central data storage unit. More particularly, the invention relates to a method and system for a managed care organization to collect and store data relating to remote medical care providers.

BACKGROUND OF THE INVENTION

Many business enterprises maintain a central data storage location whereat the bulk of the organization's business data is stored. The enterprise's business data is continuously updated by numerous employees at remote "terminals", each of which has access privileges to the central data storage unit. This known data storage model provides a central, continuously updated store of data that reflects the current state of the entire business enterprise.

The requirements for data storage and update vary widely depending on the business enterprise. For example, at one extreme, the news industry requires very flexible means of collecting data of varied and unknown format from each remote "news" site. At the other extreme, the retail store industry requires automated collection of very specific data from each remote "retail" site. However, the typical business enterprise, such as a managed care organization (MCO), collects information which is generally standardized so that the required data may be listed on some sort of questionnaire, but which may also be varied enough to require selective gathering and interpretation of the data by a human agent/surveyor.

The managed care industry requires the continuous collection and storage of data regarding the various individuals and institutions responsible for providing medical care. This data is used to ensure that the medical care providers are adhering to the standards for quality set by the managed care organization. The types of data collected can vary from organization to organization, but typically a large proportion of the data requires specific observations of the medical care provider and its practices and, therefore, must be collected at the actual location where medical care is provided. This task is usually accomplished by an agent of the managed care organization who completes a set of questions on-site and delivers the completed survey back to the MCO. The responses to the questionnaire are then processed, tabulated and reviewed by the MCO for internal purposes.

The prior art process of data acquisition from remote medical care providers can be divided into five main steps. The MCO first creates a standard questionnaire relating to the medical care provider. The MCO delivers the questionnaire to its agent/surveyor by hand-delivery, mail, or courier. The agent/surveyor completes the questionnaire at the remote medical care site such as a doctor's office or hospital. The agent/surveyor returns the completed survey to the MCO by hand-delivery, mail or courier. Finally, the MCO processes the survey by, among other things, entering the data contained in the survey into a central computer. As used herein, the term "questionnaire" refers to a set of questions and possible responses which must be filled out by a data collection agent/surveyor. As used herein, the term "survey" refers to a "questionnaire" together with the data entered by the data collection agent/surveyor.

The typical MCO uses a paper-based survey to collect information. The questions, responses, and instructions are typed on sheets of paper which must be physically transported to and from the remote medical care site. This process, as currently and widely implemented, has the inherent inefficiency that the time spent in the transmittal of information (to and from the remote medical care site) is significantly longer than the time required to collect the data from the remote medical care site. The prior art system and method also has the inherent inefficiency of duplicitive data entry and the concomitant problem of data entry error. Therefore, it is desirable to provide a system and method of collecting data from a remote medical care site wherein the data is electronically input only once at the site by a site agent/surveyor, and then electronically transferred back to the central data storage unit of the MCO.

The invention improves upon the current process of remote data collection in several ways. The method and system of the present invention eliminate the overhead associated with the production, processing, and storage of large amounts of paperwork that are required by the present process of remote data collection. The system and method also drasticly reduce the time necessary for transmitting information from the remote site to the central collecting organization, thereby reducing the time elapsed between the demand for information and the availability of the information. The system and method of the present invention also reduces the random error and costs associated with redundant data entry and hand-scoring techniques.

SUMMARY OF THE INVENTION

The present invention provides a system and method for collecting uniformly formatted data from remote sites, such as a medical care provider's office, and for electronically transmitting the data to a data storage unit at a central office of a business enterprise such as an MCO. The system and method of the present invention incorporate modern computer hardware to automate and streamline the process of data collection, transmission and storage.

The present invention also provides a method of collecting uniformly formatted data from remote sites and electronically transmitting the data back to a central site. Initially, the data to be collected from the remote site is identified. In a preferred embodiment, the data is then organized into modules. The modules and modules format are then specified. A questionnaire specification file is generated from the modules and electronically transferred to the remote data processing unit. At the remote site, the questionnaire is completed by entering the questionnaire data into the remote data processing unit. A communications link is then established between the remote data processing unit and the central unit. The data collected at the remote site is then transmitted back to the central unit for processing and tabulation.

DESCRIPTION OF PREFERRED EMBODIMENTS OF THE INVENTION

The system and method of the present invention are described below with reference to FIGS. 1–7 wherein like reference numerals are used throughout to designate like elements. The system and method of the present invention are described below in the context of the health care industry. However, one of ordinary skill in the art will recognize that the system and method of the present invention can be applied to any industry where it is necessary to collect uniformly formatted sets of data from remote sites and to transmit the data back to a central collection site.

Figure 1:
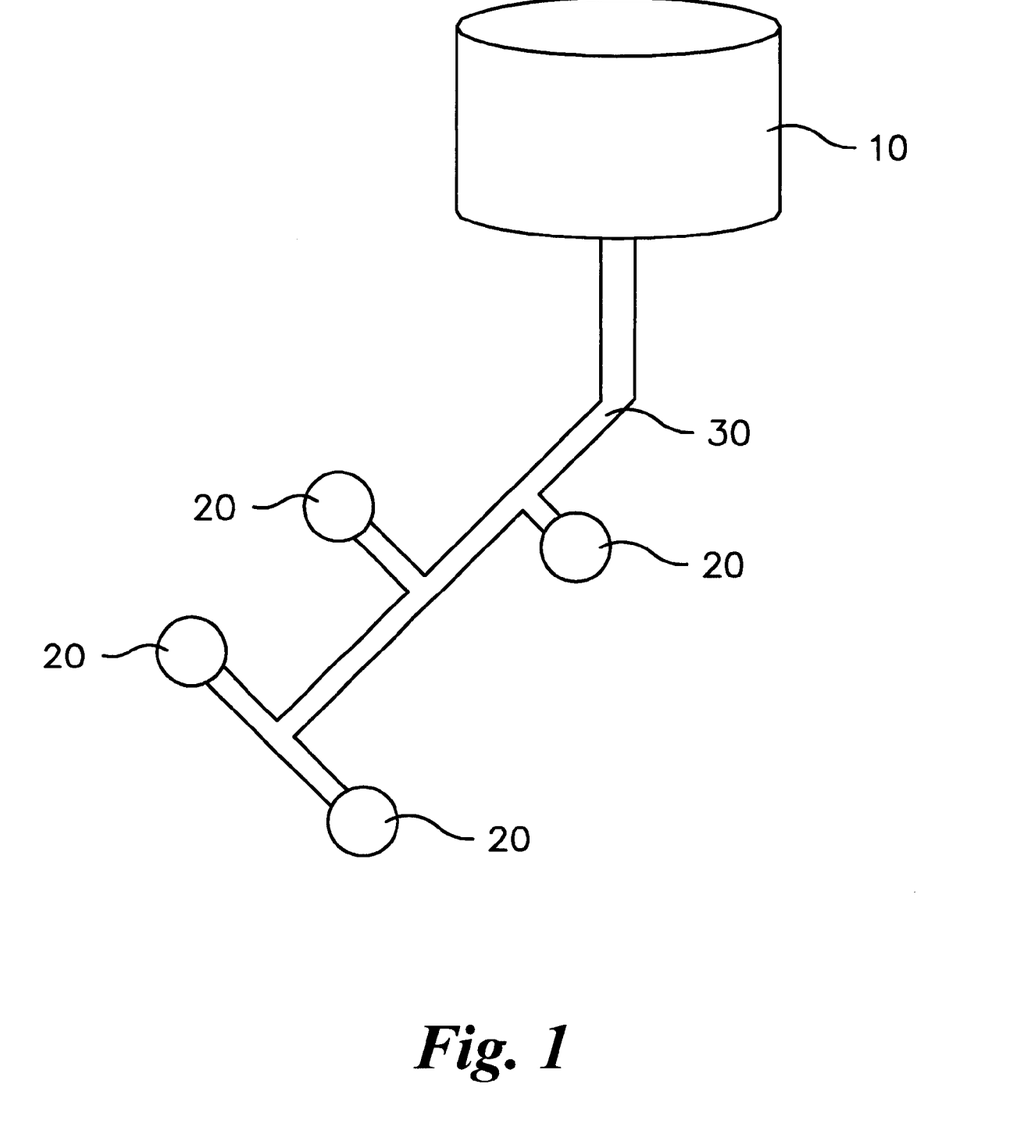
FIG. 1 is a schematic illustration of the remote data entry system in accordance with an embodiment of the invention.

Referring to FIG. 1, the system of the present invention comprises a central computing/data storage unit 10, a portable remote computing/data processing unit 20, and means for transmitting data between the central unit and the remote unit 30. The central unit 10 is a personal computer such as a Compaq Prosignia 200 running Windows NT version 4.0. The central unit 10, which may comprise more than one computer, has software which creates questionnaire specification files which specify the data to be collected, manages communication of data to and from the remote unit 20, and processes the data returned from the remote unit. The remote unit 20 is a portable, hand-held computer, preferably the PalmPilot computer manufactured by U.S. Robotics. The remote unit 20 has software which reads the question specification files generated by the central unit, allows a user to collect data in response to the questionnaire, and manages communication of data to and from the central unit. The transmitting means 30 includes a modem or HotSync™ apparatus as provided by U.S. Robotics for connecting the central unit and the remote unit to a telecommunications network such as the Internet or telephone lines. The function and operation of the above-described software are described below in the context of the method of the present invention.

Figure 2:
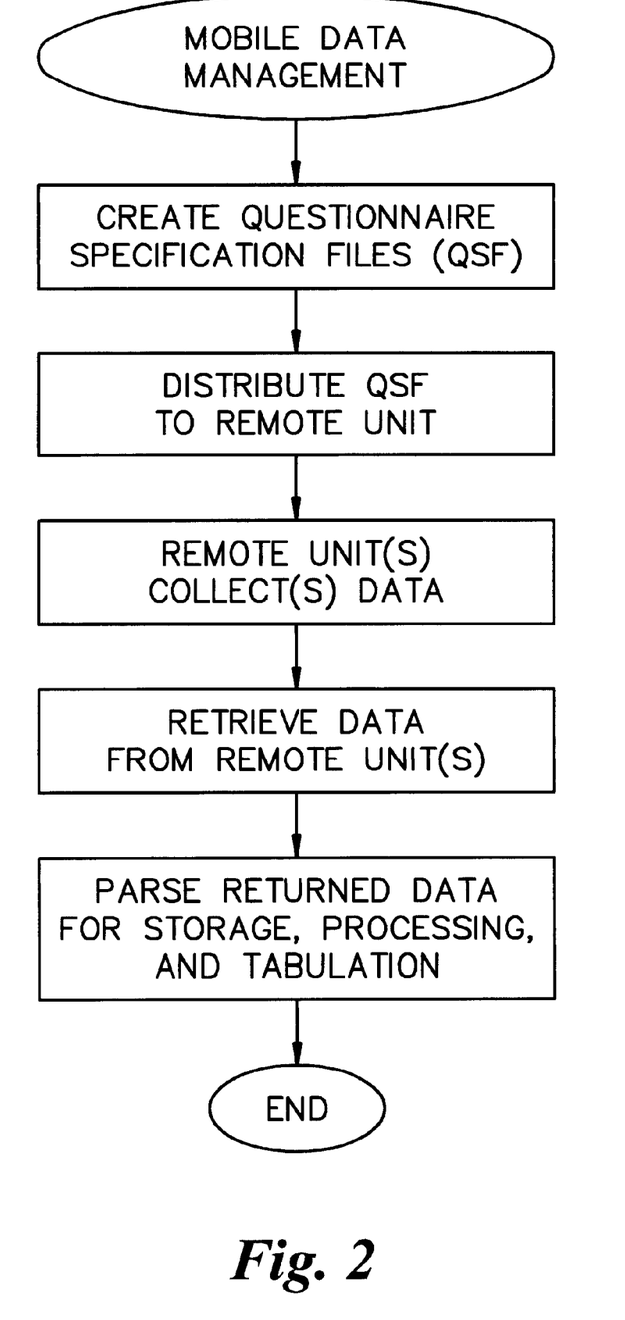
FIG. 2 is a schematic illustration of the remote data entry method in accordance with an embodiment of the invention.

The present invention provides a method of collecting uniformly formatted data from remote sites and electronically transmitting the data back to a central site. A schematic illustration of the remote data entry method of the present invention is shown in FIG. 2.

A. Creation of a Questionnaire

The initial step in the method of the present invention is to create a questionnaire which will be used by a human agent/surveyor at the remote site. The questionnaire specifies the particular data to be collected at each remote site. Since the desired data may change, the questionnaire may be updated from time to time.

Figure 3A:
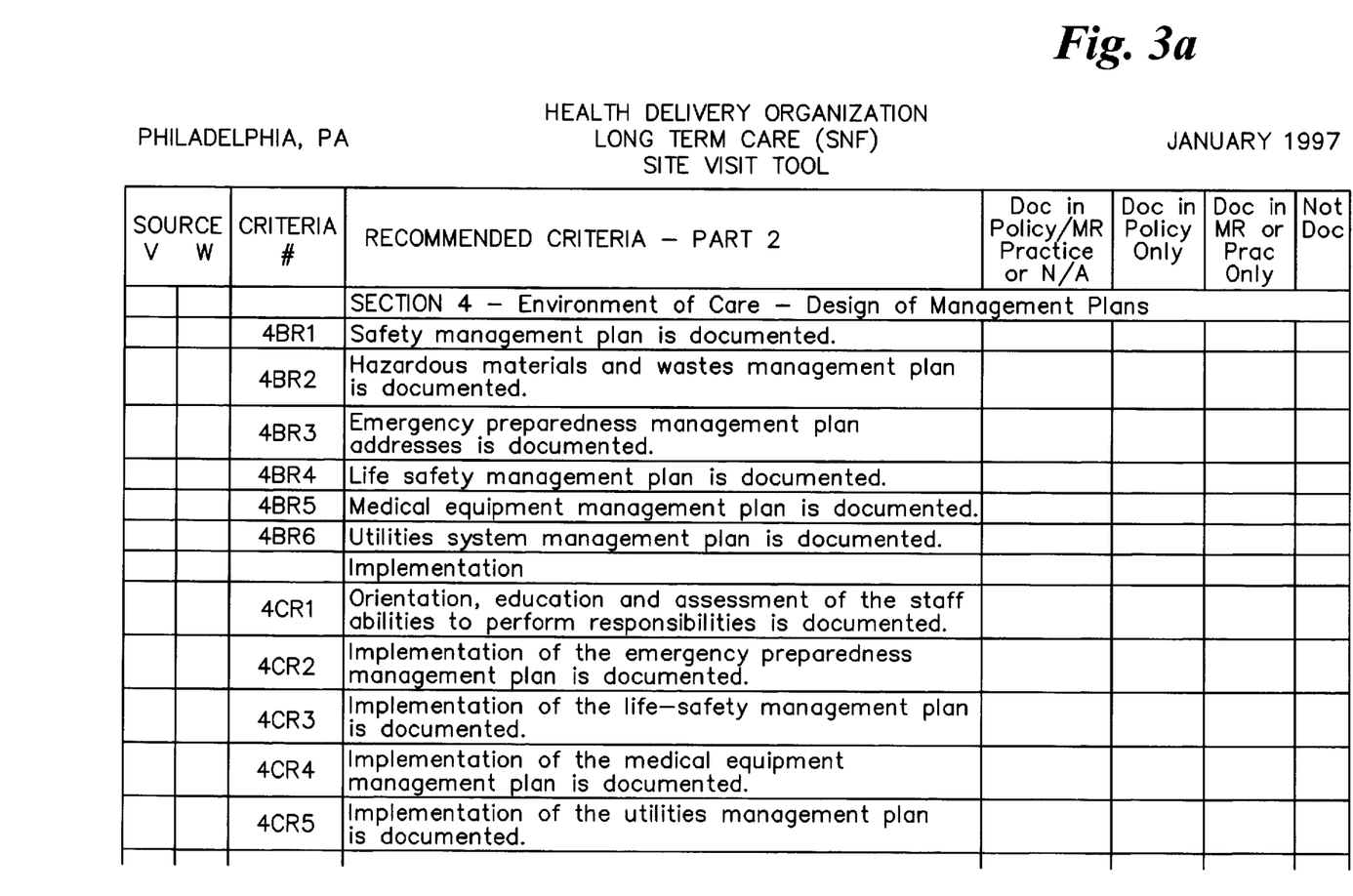
FIG. 3 is an example of a health care provider survey.
Figure 3B:
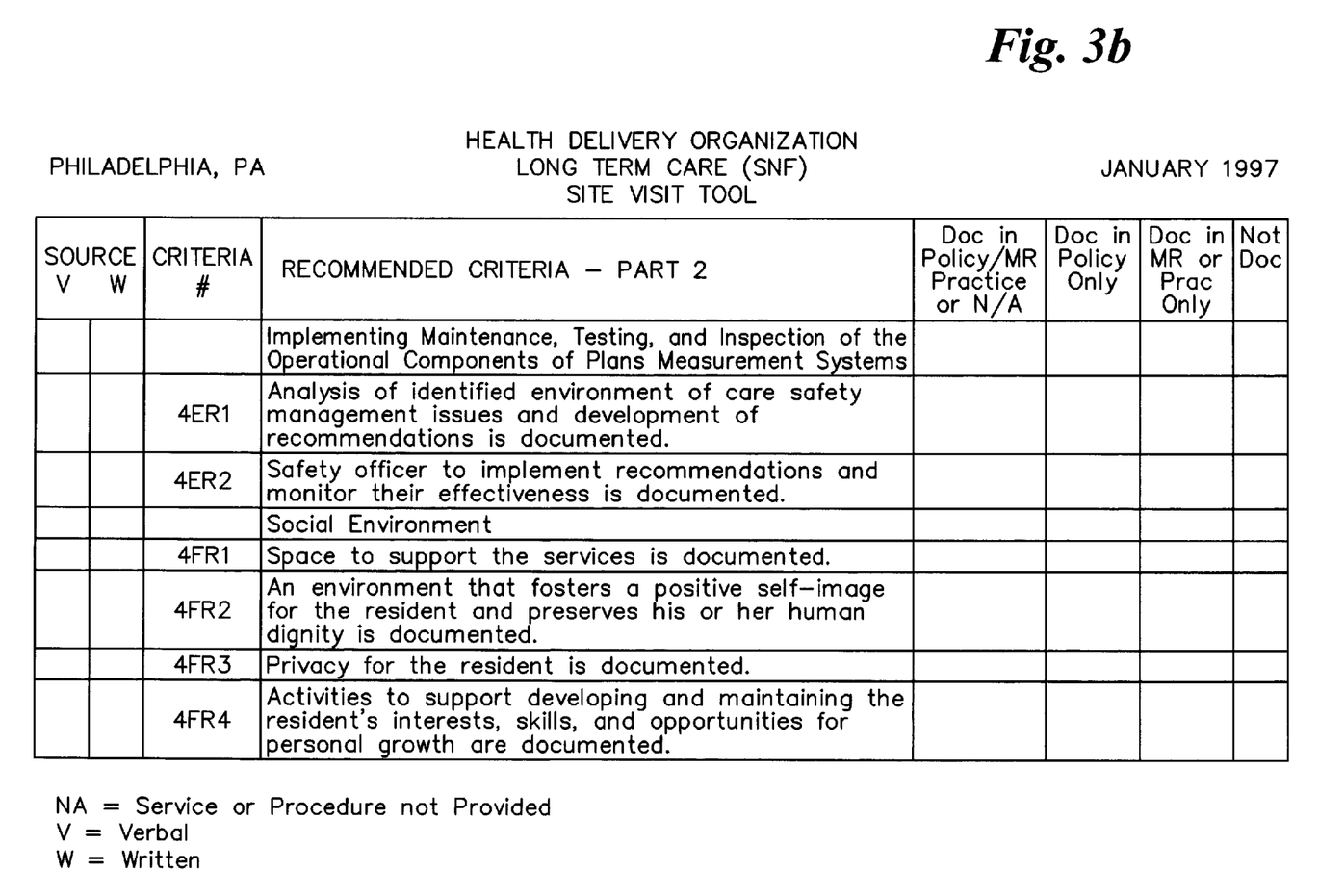

In creating the questionnaire, the data to be collected must first be identified. In the example of the managed care industry, a set of representative questionnaires is collected and analyzed for content and format. A list of survey properties common to the questionnaires is compiled. Analysis of typical health care provider questionnaires shows that the data is requested in one of two forms: (1) text data that can be represented by a sequence of letters, numbers, and punctuation; and, (2) multiple choice data that can be represented by an item chosen from a predetermined list. Analysis also shows that health care provider questionnaires are typically divided into a series of logical segments referred to herein as "modules." A module has its own type of multiple-choice data and focuses on a particular subject of inquiry in the questionnaire. As the questionnaire is performed, the surveyor initiates the module an arbitrary number of times. An example of a health care provider survey is illustrated in FIG. 3.

Figure 4:
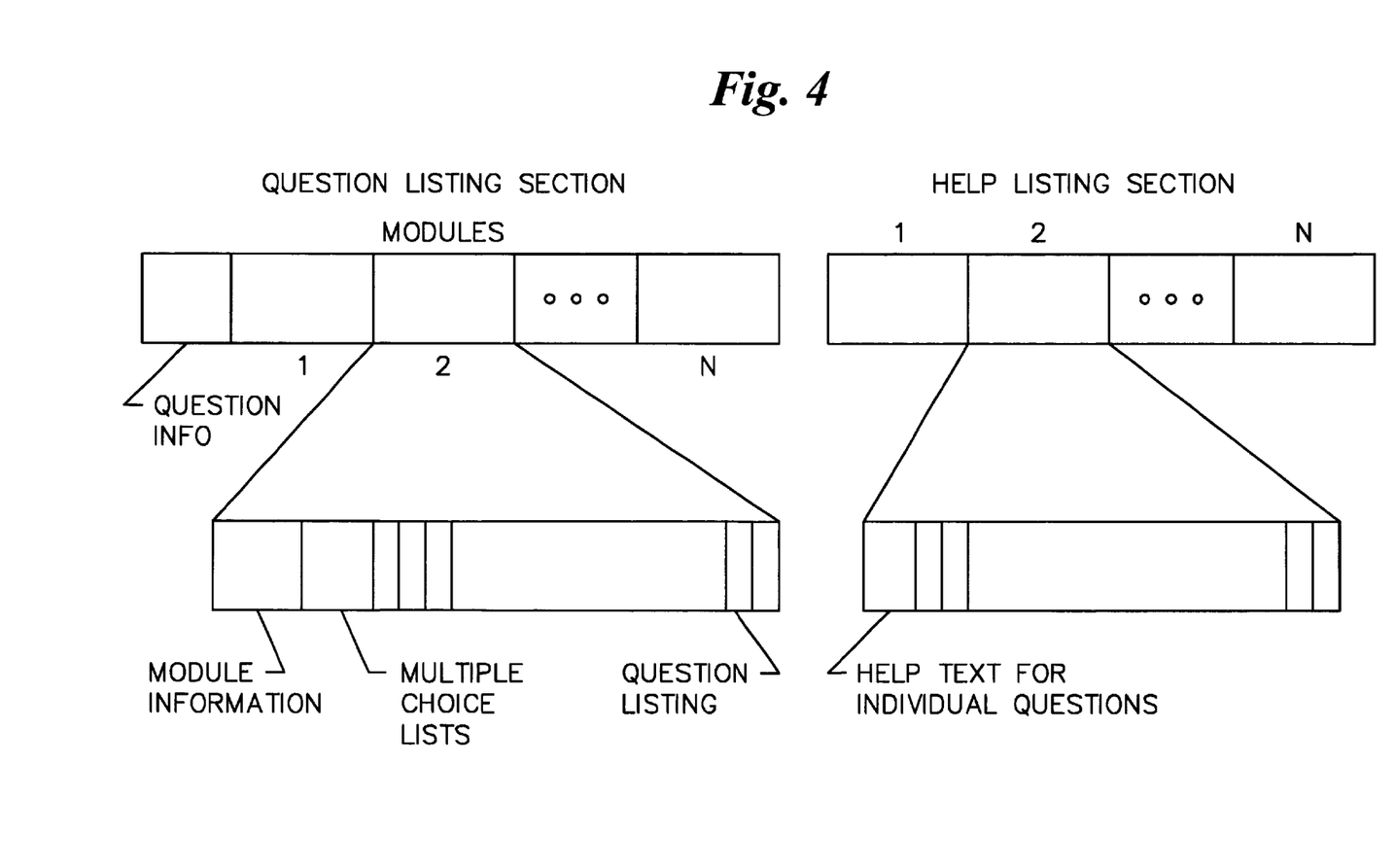
FIG. 4 is a schematic illustration of the questionnaire specification file in accordance with an embodiment of the invention.

Questionnaires used by managed care companies often require the agent/surveyor to unnecessarily repeat the data requested in some modules. For example, a "site survey" may require the agent/surveyor to complete a questionnaire for each of five different patient consulting rooms at a single provider site. In this case, certain information, such as the name and address of the provider, must be a repeated unnecessarily on each of the questionnaires. To increase efficiency, the file specification and associated abstract data structure is designed to enforce a degree of flexibility in initiating arbitrary numbers of module instances. A schematic of the questionnaire specification file of the invention is shown in FIG. 4.

A questionnaire specification data file is created based on the above-described analysis. The questionnaire creation tool (QCT) program produces a data file completely specifying the questionnaire including the various modules and their associated questions and multiple choice data formats. The questionnaire specification file (QSF) is eventually transmitted to the remote data processing unit. The questionnaire specification file can be updated to reflect changes in the questionnaire.

B. Transmission of Questionnaire to the Remote Device

After its creation, the questionnaire specification file is transmitted to the remote data processing unit over a communications network, such as telephone lines, through an adaption of the HotSync™ protocol developed by U.S. Robotics. To begin this process, the agent/surveyor attaches a modem designed for the remote data processing unit. Once the device has been properly configured, the remote unit dials the modem and opens a connection to a modem on the central data storage unit.

Once the central unit detects that a connection attempt is being made, the central unit runs various dynamically linked library's (DLLs) which independently synchronizes the databases on the central unit and the remote unit. The central unit then transmits any new questionnaire specification files to the remote unit and receives any responses to completed questionnaires from the remote unit.

In a preferred embodiment, a programming tool known as the PilotDebugger is used for the sole purpose of loading the questionnaire specification file on to the remote data processing unit. The PilotDebugger was developed by Metrowerks, Inc. and is sold as part of their CodeWarrior software development package.

Recovery of the data collected by the agent/surveyor is also preferably accomplished using the HotSync™ protocol. In a preferred embodiment, the HotSync™ protocol has been adapted to override the synchronization process and allow data to be transmitted in particular directions (for example, remote data processing unit to the central unit, or the central unit to the remote data processing unit). Since questionnaires are typically standardized and not frequently updated, adaptation of the HotSync™ protocol according to the present invention does not install questionnaire specification files but instead merely collects the data from the remote data processing unit.

A direct serial link may also be established between the remote data processing unit and the central data storage unit.

In this embodiment, the software on the central data collection unit and the remote data processing unit establish a modem connection and send the raw data over telephone lines.

Other protocols such as members of the Internet Protocol (IP) family can also be used to transmit data between the remote data processing unit and the central data storage unit. These protocols would operate on a level above that of the serial link protocols mentioned above. For example, the system may use the File Transport Protocol (FTP) member of the Telecommunications Protocol/IP (TCP/IP) family to collect data from the remote data processing unit.

In the preferred embodiment, the system utilizes the HotSync™ protocol to effect all communication between the central data storage unit and the remote data processing unit. All communication between the central unit and the remote unit occurs during the transmission process using the HotSync™ protocol.

C. Completion of the Questionnaire

Figure 5:
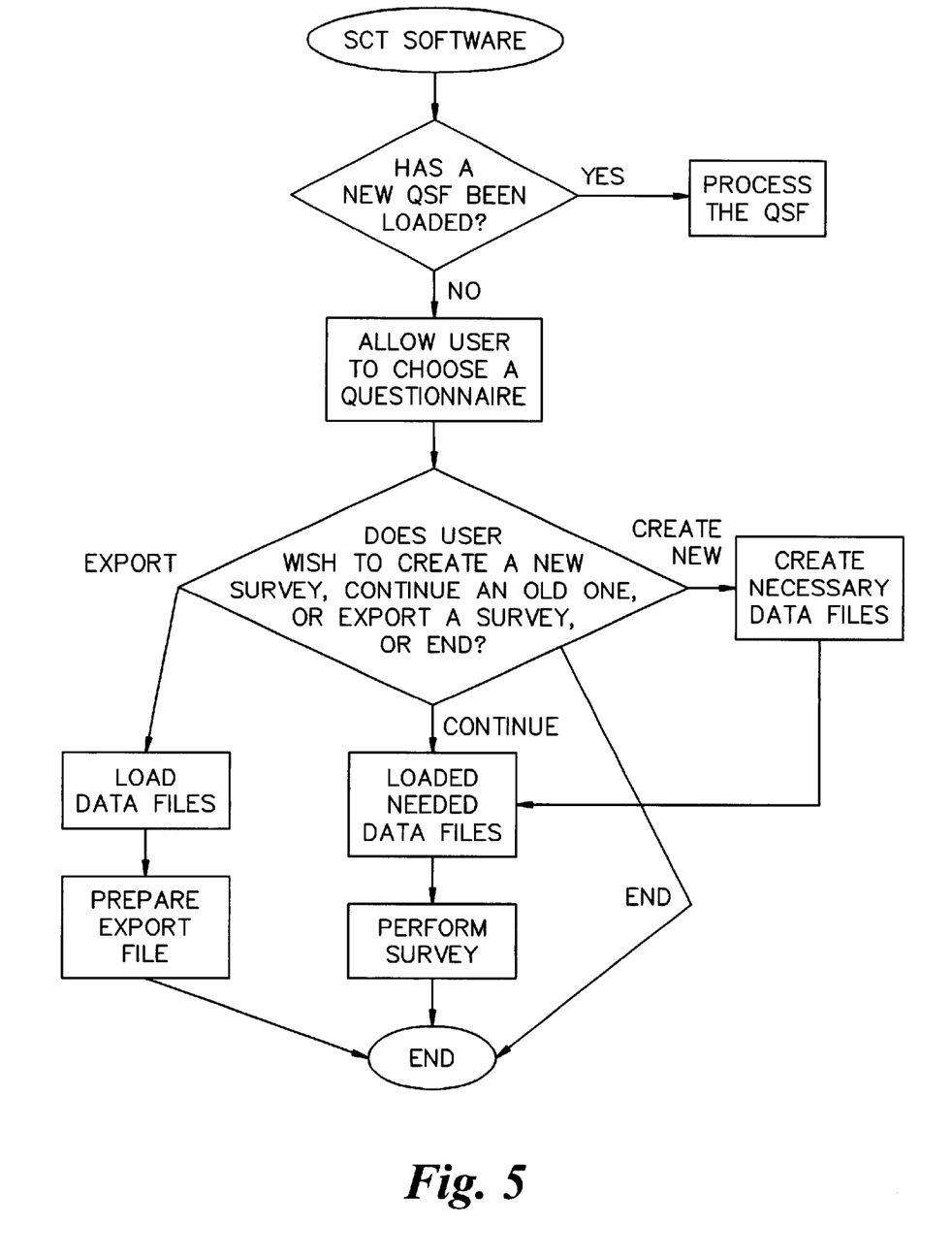
FIG. 5 is a flow diagram summarizing the main responsibilities of the survey creation tool SCT in accordance with an embodiment of the invention.

After the questionnaire has been transmitted to the remote unit, a survey creation tool (SCT) program on the remote unit creates a user interface that allows the agent/surveyor to retrieve a questionnaire based on the questionnaire specification file, enter data into the questionnaire, and navigate among the various parts of the questionnaire. The SCT program also administers (either by initiating or by preparing the data in a form ready to be sent) the communications protocol used to transmit data to and from the central unit. A flow diagram summarizing the main responsibilities of the SCT program is shown in FIG. 5.

In order to make the communications process as efficient as possible, the QSF is best transmitted as a single block of data. In contrast, the SCT program is most efficient when the QSF is broken up into smaller blocks. When the SCT program runs and determines that a QSF has been delivered to the remote device, the SCT program processes the QSF and generates a set of smaller data files for its own use. A detailed description of these files and their formats is described below.

Figure 6:
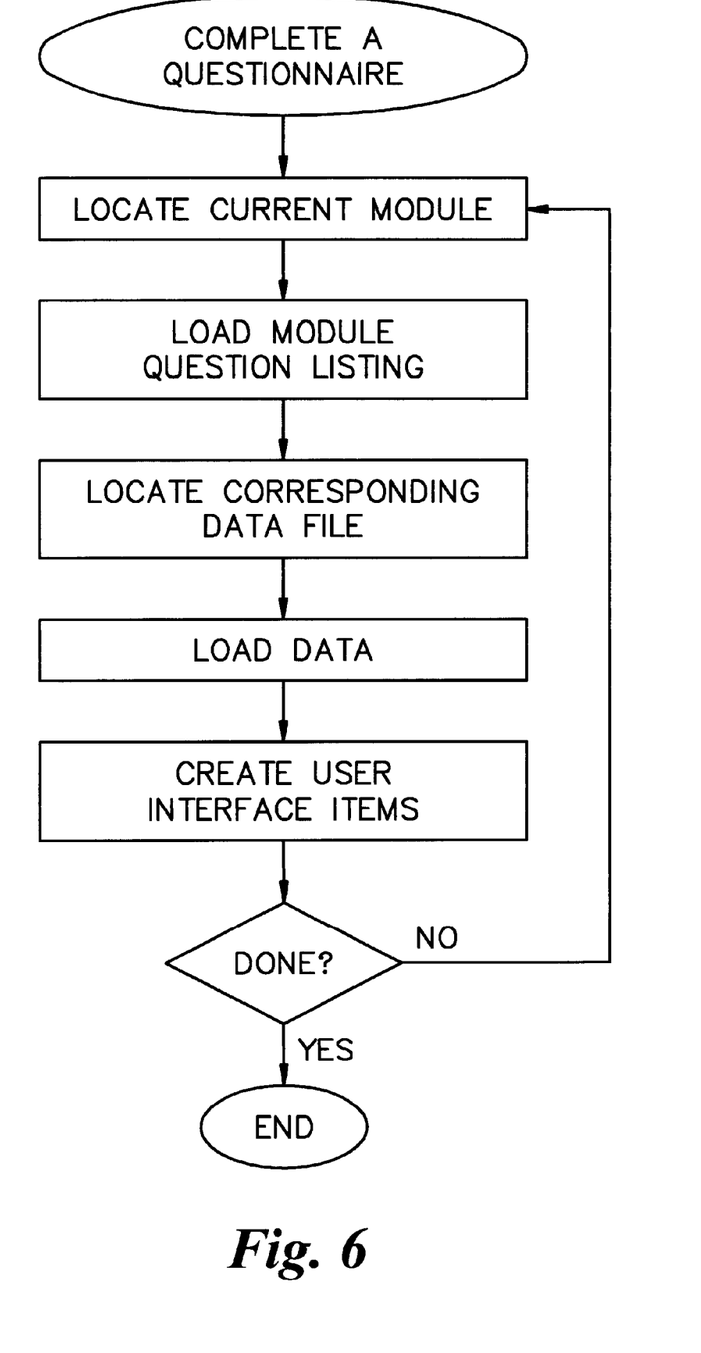
FIG. 6 is a flow diagram of the illustrating the operation process of the survey creation tool SCT in accordance with an embodiment of the invention; and, FIG. 7 is a schematic illustration of the structure of the SCT data files.
Figure 7:
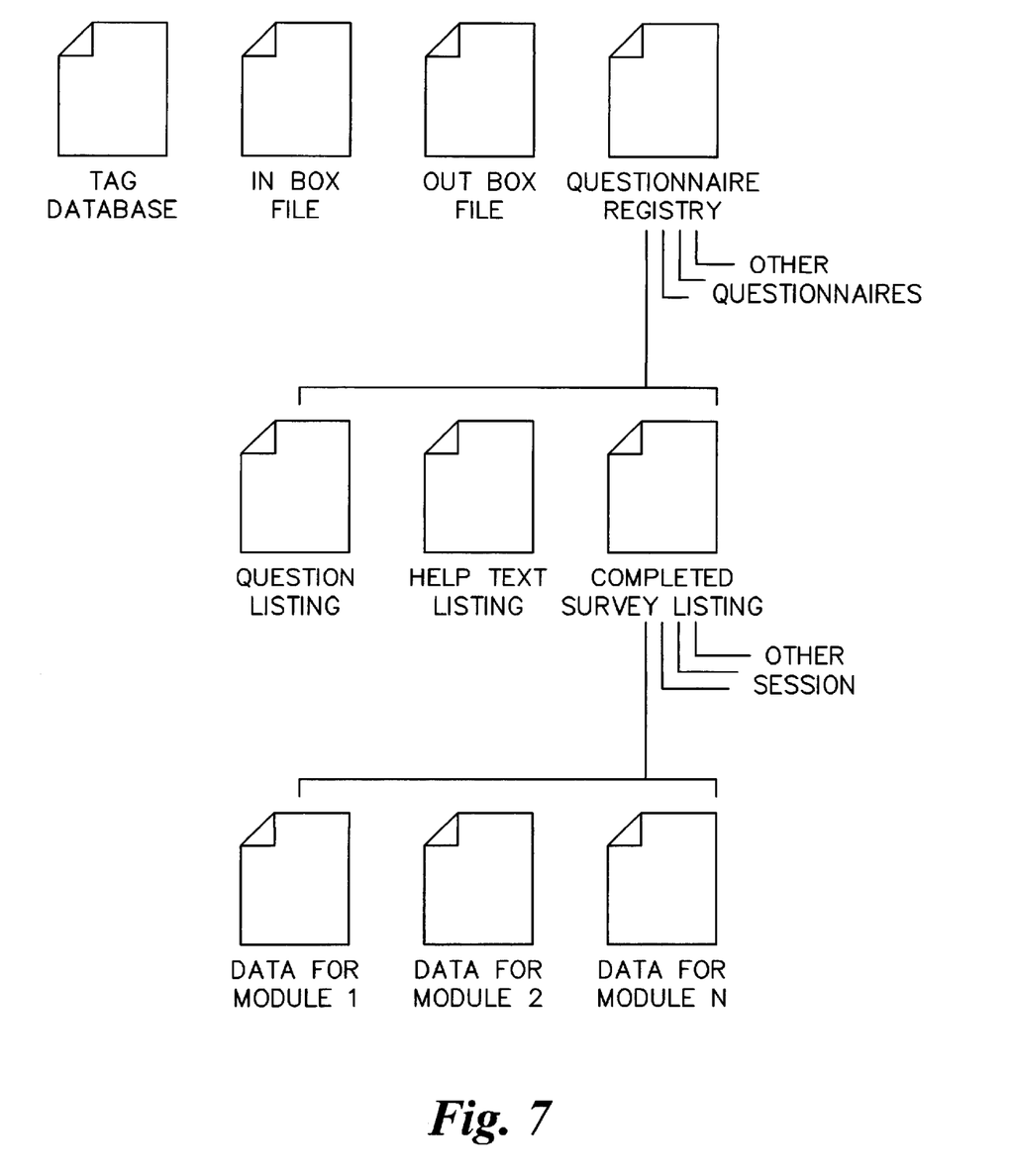

The QSF format is designed to allow the SCT program to read the questionnaire specification without constructing memory-expensive intermediate data objects. The program operation process is illustrated in FIG. 6 and involves: (1) determining which part of the questionnaire the surveyor is viewing or wishes to view; (2) determining the section of the data files which correspond to this part; and (3) displaying the relevant text or data to the screen. Given the below described formats for the relevant files, standard computing programming techniques provide all of the skills necessary to implement the SCT program.

D. Transmission of the Survey to the Central Unit

When the survey is completed, the data contained therein is transmitted back to the central unit. As described above, the SCT program initially breaks the QSF into smaller blocks for more efficient processing. The SCT program stores questionnaire data in a similar, fragmentary format. Before the data is returned to the central unit, the SCT program merges these multiple data files together to create a single data file (MCRAOutBox file) which is then transmitted to the central unit. The exported data file is then ready to be retrieved by the central unit.

E. Processing the Survey

After the survey data is returned to the central unit, the data is processed, tabulated, and stored. Before this can occur, the data must be read from the exported file and placed in a format readable by programs designed to perform said processing, tabulation, and storage. This process is accomplished in two steps: (1) the exported data file is read and represented in computer memory as an abstract data object (ADO), i.e., "parsing the data"; and, (2) creating an output file based on this ADO which can be read by the target data processing program.

Representation of the data in the ADO allows the programmer to focus on the logical structure of the data. Examples of abstract data objects include data types such as binary trees, queues, and linked lists which are familiar to those trained in computer programming. The ADO used to represent the surveys of the invention is of the "general tree" type. From an information stand point, representation of the survey as an ADO is equivalent to processing of the data.

F. Specifications for Preferred Software

The precise technical specification of the software incorporated in the present invention can, in principle, be found in its source code and associated resource files, a copy of which is attached hereto as appendix A. The function of the programs is summarized below.

1. Survey Completion Tool (SCT) Program

Filesystem Structure

The SCT program makes use of a set of files for its purposes of organizing and displaying data. A diagram showing the structure of the data files is shown FIG. 7.

Questionnaire Master Catalog

This file contains a list of all of the questionnaires currently available on the device, as well as their corresponding Tags. (See the Tag Database file description for more information on Tags)

InBox File

When a QSF is delivered to the remote unit, it is placed in the InBox file. When the SCT program starts up, it first checks this file to see if any new QSFs have appeared. New files are marked by the QCT with a two-byte sequence at the beginning of the file that instructs the program on how to handle the data in the file. (See the file format for the In box for more information).

OutBox File

The OutBox file holds all data waiting to be transmitted back to the central data collection agency. In our implementation, this is the file that the HotSync™ protocol transfers. The files in the Outfox are marked with the same two-byte code used in the In box file. (See the file format for the Inbox for more information).

Tag Database

The filesystem managed by the program is based on a file-naming scheme in which unique "tags" are added to the end of standardized file names. It is important that no Tag repeats itself to guarantee that all file names are unique. This file has a single record, which holds a value representing the next valid Tag for the filesystem. When a new file is created, this database generates a new Tag based on this record, increments the variable, and saves the variable back into the file.

Questionnaire Question Listing

This file contains the questions for a particular questionnaire. The data file takes the form of a sequence of records, each of which completely specifies exactly one module of the questionnaire.

Questionnaire Help Text Listing

The SCT program allows the creator of the questionnaire to specify help text for each question in a questionnaire. This file stores all of the help text information for a particular questionnaire.

Questionnaire Catalog

Each questionnaire in the Master Questionnaire Catalog file has an associated Questionnaire Catalog file. The Questionnaire Catalog stores information for each Session (instance) of the questionnaire, as well as the tags associated with all of the data files used by each Session.

Data Files

This is the filename for a generic data file. When the user creates a new Session, the program creates one data file per module of the questionnaire. The program then stores the responses to the questionnaire in this File.

2. File Formats Used in the System

Reserved Characters and Special Symbols

The following paragraphs explain the structure of each of the files mentioned above. The file format uses the following special characters to enforce organization on the data:

| Special Character | Hexadecimal Value |
|---|---|
| Module-Sep | 0xFC |
| Field-Sep | 0xFA |
| Record-Sep | 0xFB |

Questionnaire Master Catalog

| | |
|---|---|
| Filename: | MCRA_Questions |
| Record: | Each record registers a single questionnaire on the device |
| Structure: | Questionnaire-Name, Tag-for-Spec-Files |

InBox File

| | |
|---|---|
| Filename: | MCRA_InBox |
| Record: | Data specifying a new questionnaire or data file. The first byte specifies a "command" to be performed on the record data, the second byte is an optional argument to the command. |
| Structure: | [byte] [byte2] Record-Data |
| Notes: | Byte arrays supported have first and second bytes X and Y where |
| | 01    Create New ... |
| | 15    Reset tag |
| | Y: |
| | 01    QList File |
| | 02    QHclp File |
| | 03    Data File |
| | 0F    Null |

OutBox File

| | |
|---|---|
| Filename: | MCRA_OutBox |
| Record: | Exported data. |
| Structure: | [byte I] [byte2]Data |
| Notes: | The data is organized in Modules separated by Module-Sep characters Each Module is broken into fields separated by Field-Sep characters. Each Field is divided into Records by Record-Sep characters, each Record representing an instance Qf that particular Module. |

Tag Database

| | |
|---|---|
| Filename: | MCRA_Tags |
| Record: | Tag index |
| Structure: | Tag-Index |

Questionnaire Question Listing

| | |
|---|---|
| Filename: | MCRA__QList_[Tag] |
| Record: | Each record represents a "module" |
| Structure: | n the questionnaire Questionnaire-Name, Module-Name Number-of-Questions-in-Module = N, Number-of-Multiple-Choice-Choices= M, Choice-1, Value- 1, ... Choice-M, Value-M, Type-1, Question- I, ... Type-N, Question-N |

Questionnaire Help-Text Listing

| | |
|---|---|
| Filename: | MCRA_QHelp_[Tag] |
| Record: | Each record represents the help text for a "module" |
| Structure: | Help-Text-For-Question- 1, ..., Help-Text-For-Question-N |

Questionnaire Catalog

| | |
|---|---|
| Filename: | NCRA_QCatalog_[Tag] |
| Record: | Data for a single session of the current questionnaire |
| Example: | Session-Name, Lock-Status, Start-Date, Completion-Date, Process-Date, Export-Date, Tag-for-Data-File-For-Module-1, Tag- for-Data-File-For-Module-N |

Data File

| | |
|---|---|
| Filename: | MCRA_[Tag] |
| Record: | Each record is a single instance of a single module. |
| Structure: | Data-For-Question- 1 ..., Data-For-Question-N, |

What is claimed is:

1. A system for collecting uniformly formatted sets of data from a remote site and electronically transmitting the data to a central collection site, comprising:
   a) a central computing/data storage unit having:
      i) means for creating a questionnaire specification file, the questionnaire specification file defining the file specification and associated data structure for creating questionnaires;
      ii) means for managing communication to and from the remote unit; and
      iii) means for processing data returned from the remote unit;
   b) remote computing/data processing unit having:
      i) means for receiving and reading a questionnaire specification file;
      ii) means for creating at least one questionnaire from the defined file specification and associated data structure in the questionnaire specification file;
      iii) means for collecting data in response to the presentation of the questionnaire; and
      iv) means for managing communication of data to and from the central unit; and,
   c) means for transmitting data between said central unit and said remote unit.

2. The system recited in claim 1, said means for creating a questionnaire specification file including means for creating data modules within the questionnaire specification file.

3. The system recited in claim 1, including means for modifying the questionnaire specification file to reflect updates in the data to be collected by the questionnaire.

4. The system recited in claim 1, said means for managing communication to and from said remote unit comprising a dynamically linked library which independently synchronizes databases on the central unit and remote unit.

5. The system recited in claim 4, said dynamically linked library designed to work with U.S. Robotic's HotSync™ protocol.

6. The system recited in claim 4, including means for establishing a direct serial link between the central unit and the remote unit.

7. The system recited in claim 4, said dynamically linked library designed to work with the File Transport Protocol (FTP) member of the Telecommunications Protocol/IP (TCP/IP).

8. The system recited in claim 1, said processing means including means for reading, interpreting and tabulating data returned to said central unit.

9. The system recited in claim 1, including means for connecting said central unit and said remote unit to a communications network.

10. The system recited in claim 1, said remote unit comprising a PalmPilot™ portable computer.

11. The system recited in claim 1, said reading means comprising the PilotDebugger™ software.

12. The system recited in claim 1 wherein the remote unit further includes:
   means for creating a user interface using the questionnaire specification file, the user interface allowing a user to retrieve a questionnaire, enter data into the questionnaire, and navigate within the questionnaire.

13. The system recited in claim 12, including means for processing the questionnaire specification file into a set of data files.

14. The system recited in claim 13, including means for identifying a particular module of the questionnaire, identifying the data file corresponding to said module, and displaying the text and data from said module on the remote unit.

15. The system recited in claim 14, including means for merging said set of data files after completion of the questionnaire.

16. The system recited in claim 1, said processing means including means for reading and representing the data as an abstract data object and creating an output file based on the abstract data object which can be read by a target data processing program.

17. A method of collecting uniformly formatted sets of data from a remote site and electronically transmitting the data back to a central collection site, comprising the steps of:
   a) specifying the data to be collected;
   b) generating a questionnaire specification file, the questionnaire specification file defining the file specification and associated data structure for creating questionnaires;
   c) establishing a telecommunications link between a central computing/data processing unit at the central collection site and a remote computing/data processing unit at the remote site;
   d) electronically transmitting the questionnaire specification file to the remote data processing unit;
   e) in the remote unit, using the defined file specification and associated data structure in the questionnaire specification file to create at least one questionnaire;
   f) completing the questionnaire at the remote site by entering questionnaire data into the remote unit; and
   g) transmitting the data in report format back to the central unit at the central collection site.

18. The method recited in claim 17, wherein the step of specifying the data includes:
   i) dividing the data into modules; and,
   ii) specifying the modules and the module format.

19. The method recited in claim 17, including the step of collecting a set of representative survey forms and compiling a list of properties common to the survey forms.

20. The method recited in claim 17, including the steps of modifying the questionnaire specification file to reflect updates in the data to be collected by the questionnaire.

21. The method recited in claim 17, including the step of creating data modules within the questionnaire specification file.

22. The method recited in claim 17, including the step of independently synchronizing databases on the central unit and remote unit.

23. The method recited in claim 22, said databases synchronized using the U.S. Robotic's HotSync™ protocol.

24. The method recited in claim 22, including the step of establishing a direct serial link between the central unit and the remote unit.

25. The method recited in claim 22, said databases synchronized using the File Transport Protocol (FTP) member of the Telecommunications Protocol/IP (TCP/IP).

26. The method recited in claim 17, including the step of reading, interpreting and tabulating the data returned to the central unit.

27. The method recited in claim 17 wherein step e) further comprises using the questionnaire specification file to create a user interface that allows a user to retrieve a questionnaire, enter data into the questionnaire, and navigate within the questionnaire.

28. The method recited in claim 17, including the step of processing the questionnaire specification file into a set of data files in the remote unit.

29. The method recited in claim 28, including the step of identifying a particular module of the questionnaire, identifying the data file corresponding to said module, and displaying the text and data from said module on the remote unit.

30. The method recited in claim 29, including the step of merging said set of data files after completion of the questionnaire.

31. The method recited in claim 17, including the step of reading and representing the data as an abstract data object and creating an output file based on the abstract data object which can be read by a target data processing program.

32. A method of collecting uniformly formatted sets of data from remote medical care provider sites and electronically transmitting the data back to a managed care organization, comprising the steps of:
   a) specifying the data to be collected from the provider;
   b) dividing the data into modules;
   c) specifying the modules and the module format;
   d) generating a questionnaire specification file, the questionnaire specification file defining the file specification and associated data structure for creating questionnaires;
   e) establishing a telecommunications link between a central computing/data processing unit at a managed care organization and a remote computing/data processing unit at the remote site;
   f) electronically transmitting the questionnaire specification file to the remote data processing unit;
   g) in the remote unit, using the defined file specification and associated data structure in the questionnaire specification file to create at least one questionnaire;

h) completing the questionnaire at the remote site by entering questionnaire data into the remote unit;

i) transmitting the data back to the central unit at the managed care organization.

33. The method recited in claim 32, including the steps of:

i) modifying the questionaire specification file to reflect updates in the data to be collected by the questionnaire;

j) reading the questionnaire specification file and creating a questionnaire user interface on the remote unit;

k) creating data modules within the questionnaire specification file;

l) independently synchronizing databases on the central unit and remote unit using the U.S. Robotic's HotSync™ protocol or the File Transport protocol (FTP) member of the Telecommunications Protocol/IP (TCP/IP), or establishing a direct serial link between the central unit and the remote unit;

m) reading, interpreting and tabulating the data returned to the central unit;

n) creating a user interface that allows a user to retrieve a questionnaire based on the question specification file, entering data into the questionnaire, and navigating within the questionnaire;

o) processing the questionnaire specification file into a set of data files;

p) identifying a particular module of the questionnaire, identifying the data file corresponding to said module, and displaying the text and data from said module on the remote unit;

q) merging said set of data files after completion of the questionnaire; and, r) reading and representing the data as an abstract data object and creating an output file based on the abstract data object which can be read by a target data processing program.

34. A method of providing at least one questionnaire at a remote site comprising:

a) at a central site, specifying the data to be collected by the questionnaire;

b) at the central site, generating a questionnaire specification file, the questionnaire specification file defining the file specification and associated data structure for creating questionnaires;

c) establishing a telecommunications link between the central site and a remote computing/data processing unit at the remote site;

d) electronically transmitting the questionnaire specification file to the remote data processing device; and e) in the remote unit, using the defined file specification and associated data structure in the questionnaire specification file to create at least one questionnaire.

35. The method of claim 34 further comprising:

f) completing the questionnaire at the remote site by entering questionnaire data into the remote unit; and g) transmitting the data in report format back to the central unit at the central collection site.

36. An apparatus for providing at least one questionnaire at a remote site comprising:

a) at a central site, means for specifying the data to be collected by the questionnaire;

b) at the central site, means for generating a questionnaire specification file, the questionnaire specification file defining the file specification and associated data structure for creating questionnaires;

c) means for establishing a telecommunications link between the central site and a remote computing/data processing unit at the remote site;

d) electronically transmitting the questionnaire specification file to the remote data processing device; and e) in the remote unit at the remote site, means for using the defined file specification and associated data structure in the questionnaire specification file to create at least one questionnaire.

37. The apparatus of claim 36 further comprising:

f) means for completing the questionnaire by entering questionnaire data into the remote unit; and g) means for transmitting the data in report format from the remote unit to the central unit.

* * * * *